United States Patent [19]

Rathbone et al.

[11] Patent Number: 4,703,761
[45] Date of Patent: Nov. 3, 1987

[54] BLOOD SAMPLING DEVICE FOR OBTAINING SMALL QUANTITY OF VENOUS BLOOD

[76] Inventors: R. Rodion Rathbone, Hamden; Stephen C. Wardlaw, Branford, both of Conn.; R. Rodion Rathbone, 1800 Whitney Ave., Hamden, Conn. 06514; Stephen C. Wardlaw, 128 Sunset Hill Dr., Branford, Conn. 06405

[21] Appl. No.: 892,265

[22] Filed: Aug. 4, 1986

[51] Int. Cl.$^4$ ............................................... A61B 5/00
[52] U.S. Cl. ................................... 128/763; 128/770; 604/236; 604/406
[58] Field of Search .............................. 128/763–768, 128/770; 604/126, 167, 215, 236–238, 264, 272, 403, 406, 410, 411, 414

[56] References Cited

U.S. PATENT DOCUMENTS

| | | | |
|---|---|---|---|
| 2,727,516 | 12/1955 | Lockhart | 128/765 |
| 3,604,410 | 9/1971 | Whiteacre | 128/764 |
| 3,648,684 | 5/1972 | Barnwell et al. | 128/764 |
| 3,706,305 | 12/1972 | Berger et al. | 128/762 |
| 3,908,638 | 9/1975 | Porcher et al. | 128/763 |
| 4,020,831 | 5/1977 | Adler | 128/765 |
| 4,187,860 | 2/1980 | Villari | 128/763 |
| 4,385,637 | 5/1983 | Akhair | 128/763 |
| 4,398,544 | 8/1983 | Nugent et al. | 604/236 |

*Primary Examiner*—William E. Kamm
*Assistant Examiner*—Max F. Hindenburg
*Attorney, Agent, or Firm*—William W. Jones

[57] ABSTRACT

This device is adapted for taking venous blood samples without the aid of any auxiliary negative pressure. Venous blood pressure is the sole force which fills the device with the blood sample. The device includes a flexible plastic tube formed from polyethylene or the like and further includes a blood drawing needle mounted on one end of the tube. The tube is divided into a collection reservoir into which the sample is drawn, and a sampling reservoir into which the sample may be expressed from the collection area. A valve separates the two areas. Also included in an elastomeric needle closure which adapts the device for in situ centrifugation of the blood sample in a test tube.

20 Claims, 12 Drawing Figures

BLOOD SAMPLING DEVICE FOR OBTAINING SMALL QUANTITY OF VENOUS BLOOD

This invention relates to a device for drawing blood samples solely under venous pressure. No auxiliary negative pressure needs be used to draw the blood into the device of this invention.

Blood samples may be drawn by means of a number of different procedures and paraphenalia. For example, blood may be drawn using a capillary tube finger stick when only small samples are needed. Larger samples are generally taken with pre-evacuated tubes which operate with needles which penetrate the vein. The contained vacuum within the tube then causes the blood to be drawn quickly into the tube. Illustrative of this manner of drawing blood is the disclosure of U.S. Pat. No. 4,187,861 to B. T. Heffernan.

Another way of drawing blood which is disclosed in the prior art utilizes arterial blood pressure as the force which causes the blood to flow into the collecting device. This type of device uses a collecting tube made from plastic, or the like, a needle at one end of the tube, and an air pressure relief valve at the other end of the tube. The valve is in the form of a non-wetting filter disk which allows passage of air but prevents passage of blood. When the sample is taken, arterial blood pressure forces the blood into the collection tube and air is forced out of the tube via the filter disk. The filter disk is impermeable to blood so that the device will not accept further blood, once filled. This technique is described in U.S. Pat. Nos. 4,266,558; 4,266,559; 4,317,455; and 4,367,754 all to D. S. Akhavi.

Still another procedure for drawing blood disclosed in the prior art involves the use of a flexible plastic collection reservoir which is connected to a collecting tube and which is manually squeezed to create negative pressure for drawing the blood sample. These devices operate in a manner similar to an eye dropper. Such devices are shown in U.S. Pat. Nos. 3,513,829 to Deuschle et al; 4,411,163 to White; and 4,250,893 to White. Conventional syringes may also be used to draw blood.

The devices in the prior art which utilize arterial blood pressure and/or manually created negative pressure to create the flow of blood into the collection reservoir also use the needle or the collection tube as the means for expressing the blood from the device. This means that the collection device cannot be used as a vehicle for certain procedures, as, for example, centrifugation. This also means that the needle is exposed and may accidentally stick someone. It should be noted that the needle may be contaminated with infectious agents.

Devices which are pre-evacuated to take blood samples are uncorked to remove the blood for testing. The blood can be drawn out with a capillary tube, pipette or may be poured out. The blood sample may be centrifuged in the evacuated collection tube, and the centrifuged components can then be drawn out of the tube for analysis.

The device of this invention utilizes venous blood pressure, which may be augmented by a tourniquet, to allow the sample to flow into the collection reservoir. The device includes an elastomeric tubular member which receives the blood sample. The tubular member is connected to a needle-bearing base which is a relatively rigid material. A valve member is positioned in the tubular member remote from the base. The valve is initially closed so as to allow passage of air but block passage of blood. The valve can also be opened after the sample is obtained so as to allow blood to be expressed or withdrawn from the device. The device may also include a sampling portion which is downstream of the valve and into which blood or blood components can be expressed from the collection portion. Also included is a needle closing member which takes the form of a contoured body formed from an elastomeric material. The needle is pressed into the needle closing member, and the latter is adapted to interlock with the needle-bearing base of the device. In this manner, the needle is both sealed and safely shielded. Once the needle is sealed, blood or blood components can be removed from the device via the valved end of the device. The needle closing member is formed so as to fit snugly into the bottom of a test tube in which the device is stored. This adapts the device for in-situ centrifugation of the blood sample. The device of this invention can also be formed in a duplex embodiment wherein multiple blood samples can be drawn. The duplex components can be differentiated so that one sample can be whole blood and the other can be anticoagulated blood. The duplex embodiment can be formed as a one-piece device which can be later separated into individual components, if desired.

It is, therefore, an object of this invention to provide a blood sampling device which can utilize venous blood pressure as the sole force which causes blood to flow into the device.

It is a further object of this invention to provide a blood sampling device of the character described which includes a valve which is closed to allow passage of air from the device during drawing of the blood sample and which may be opened to allow passage of blood or blood components.

It is yet another object of this invention to provide a blood sampling device of the character described which has an optional sampling reservoir downstream of the collection reservoir from which specimens can be removed.

It is an additional object of this invention to provide a blood sampling device of the character described which has a needle plug adapted to be locked to the remainder of the device and which adapts the device for in-situ centrifugation of the blood sample.

These and other objects and advantages of the device of this invention will become more readily apparent from the following detailed description of preferred embodiments of the invention when taken in conjunction with the accompanying drawings, in which:

FIG. 3 is a sectional view showing the device with the needle plugged and the valve opened as a specimen is expressed from the collection reservoir to the sampling reservoir and drawn therefrom into a capillary tube, or the like;

Figure 1:
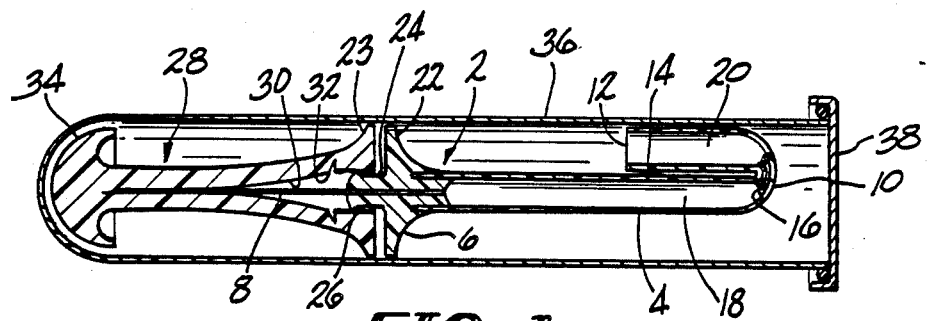
FIG. 1 is an axial sectional view of a preferred embodiment of a blood sampling device formed in accordance with this invention, the device being shown in its containing tube preparatory to being used for drawing a blood sample.

Referring now to the drawings, there is shown in FIG. 1 a preferred embodiment of a device formed in accordance with this invention, which device includes a blood collecting member denoted generally by the numeral 2. The member 2 comprises an elastomeric tubular part 4, which is mounted on a relatively rigid base 6. A blood collecting needle 8 extends through the base 6 and opens into the tubular part 4. The tubular part 4 is kinked at 10 and the free end 12 of the tube 4 is releasably adhered to the remainder of the tube at 14 to maintain the kink 10. A filter valve 16 is positioned inside the tube 4 in the kink to keep the bore of the tube 4 open to passage of air. The valve 16 is formed from a hydrophobic porous material such as filamentous HDPE, Whatman phase-separation paper, or the like. The valve serves to hold the bore of the tube 4 open inside the kink 10 so as to allow air to vent from the tube 4 as the blood sample is drawn. Blood will not pass through the valve 16 so long as the tube remains kinked. The device can operate to draw a blood sample solely through the use of venous blood pressure when the vein is subjected to a tourniquet. The kink 10 divides the tube 4 into a collection chamber 18, into which the needle 8 opens, and a sampling chamber 20 downstream of the valve 16. The sampling chamber may be relatively long, as illustrated, or shortened to allow a dropper-like action when blood is expressed from the collection reservoir. The base 6 includes a radial flange 22 for gripping and an axial boss 24 having a circumferential locking rib 26 formed thereon. The device also includes a plug 28 formed from an elastomeric material. The plug 28 has a tapered blind bore 30 and is initially frictionally fitted onto the boss 24 so that the plug 28 serves to protect the needle 8 prior to use of the device. To use the device, the collector 2 is pulled out of the plug 28. The bore 30 includes a locking groove 32 formed therein. The plug 28 also includes a flange 23 and an enlarged foot 34 having an outer surface which is contoured to fit into the bottom of the tube 36 in which the device is packaged. A cap 38 is fitted onto the open end of the tube 36 to close the latter and keep the device sterile prior to use. It will be noted that the flanges 22 and 23 closely fit inside the tube 36. In this manner, the foot 34 and the flanges 22 and 23 provide sufficient support for the device that a blood sample can be centrifuged in the tube 4 after being drawn, once the device is reinserted into the container tube 36.

Figure 2:
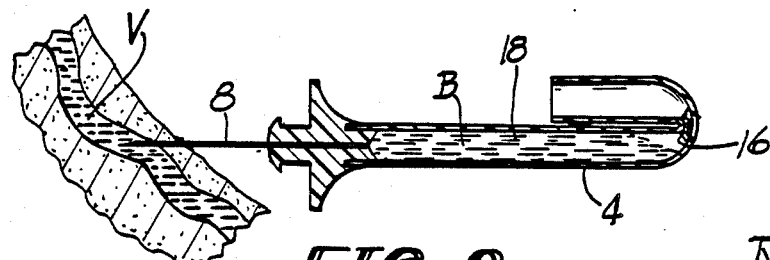
FIG. 2 is a sectional view of the device of FIG. 1 shown drawing a blood sample.
Figure 3:
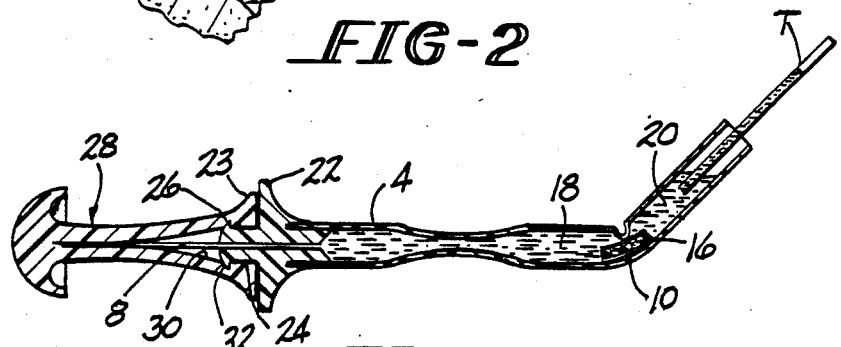

Referring to FIGS. 2 and 3, the manner in which the device is used is illustrated. With the arm under tourniquet pressure, a vein V is punctured by the needle 8. Venous blood pressure causes blood B to flow into the tube 4. Air is expelled from the collection chamber 18 through the valve 16. Once the blood reaches the valve 16, flow stops as the blood is unable to pass by the valve 16. The needle 8 is then withdrawn from the vein V and is then inserted into the bore 30 of the plug 28. The needle 8 is pressed into the plug 28 until the flanges 22 and 23 abut and the rib 26 locks into the groove 32. At this point, the needle 8 is locked in the plug 28, is sealed, and cannot be withdrawn from the bore 30. If desired, the filled device can be reinserted into the container tube 36 and the blood sample can be centrifuged in-situ so as to layer out the blood constituents in the tube 4. In this event, the plasma or serum constituent layer would be closest to the valve 16. The valve 16 is opened by breaking the adhesive bond 14 and relieving the kink 10, as shown in FIG. 3. In this mode, a portion of the sample may be expressed from the collection chamber 18 through the valve 16 into the sampling chamber 20 by squeezing the tube 4 with the fingers. A tube T such as a capillary tube or a pipette x-ray be inserted into the sampling chamber 20 to draw a sample therefrom. It should be noted that the tube T can also be inserted into the collection chamber 18 past the valve 16 if desired. In this manner, a blood sample can be taken, or if the blood has been centrifuged in the device, a plasma or other constituent sample can be drawn into the tube T.

Figure 4:
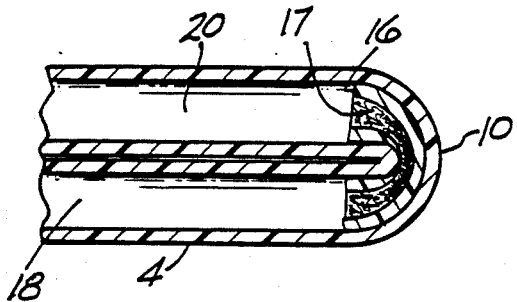
FIG. 4 is a fragmented sectional view enlarged for clarity, showing the valve in its closed condition wherein air will pass but blood will not pass therethrough.
Figure 5:
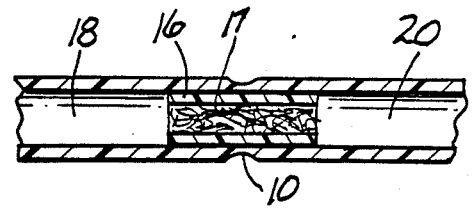
FIG. 5 is a fragmented sectional view similar to FIG. 4 but showing the valve open to passage of blood or a blood drawing instrument, such as a capillary tube.

Referring to FIGS. 4 and 5, one specific form of valve 16 is shown. This form of the valve 16 is a hollow cylinder of the porous hydrophobic material which has a through passage 17. When the tube 4 is kinked, the valve cylinder 16 is also kinked to close off its through passage 17 as shown in FIG. 4. The collapsed walls of the valve cylinder 16 are porous to the passage of air and they hold the sides of the bore of the tube 4 away from each other so that air can vent through the kink. The hydrophobic nature of the valve material prevents blood from passing through the kink. When the kink 10 is released, as shown in FIG. 5, the through passage 17 of the cylinder valve 16 opens up and blood can be expressed through it, or a sampling tube can be inserted through it. Thus, communication is established between the collection chamber 18 and the sampling chamber 20.

Figure 6:
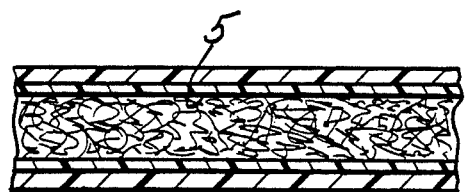
FIG. 6 is a fragmented sectional view of an alternative embodiment of a tube which may be used to form the device of this invention.

In lieu of a finite valve cylinder, the tube 4 can be formed with a coextruded lining 5 of the hydrophobic porous material, as shown in FIG. 6. This embodiment will operate as described above.

It is also possible to use a strip or disk of the hydrophopic porous material which will be trapped in the kink but, once the kink is relaxed, can move out of the way to open the bore of the tube 4.

Figure 7:
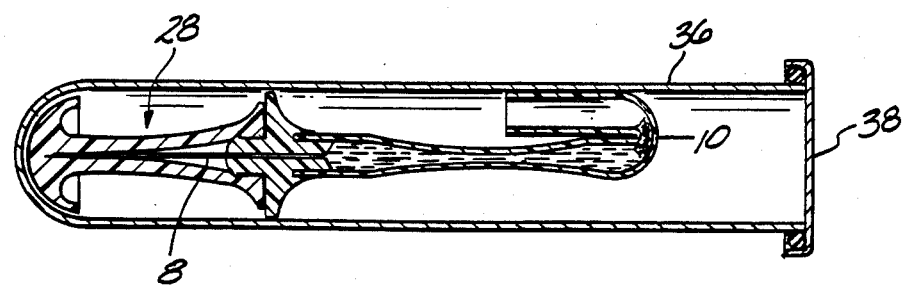
FIG. 7 is a sectional view of the device similar to FIG. 1 but showing the device after it has been substantially depleted of blood and preparatory to being discarded.

Referring to FIG. 7, the manner of disposing of the used device is shown. The device with its needle 8 safely locked inside the plug 28 and the majority of the blood depleted is rekinked and reinserted into the container tube 36. The container tube 36 is then reclosed, and the device is safely discarded.

Figure 8:
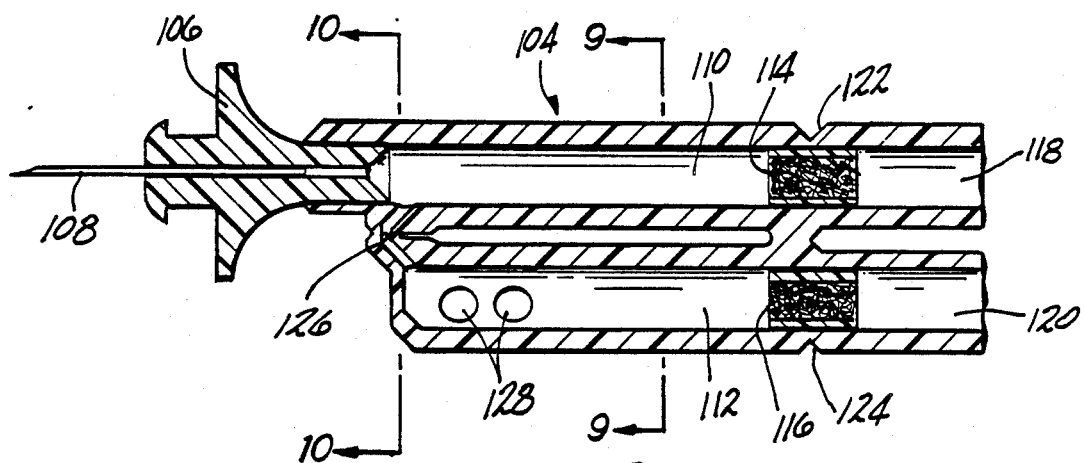
FIG. 8 is a sectional view of a duplex embodiment of the sampling device of this invention which may be used for drawing whole and anticoagulated blood samples in series.
Figure 10:
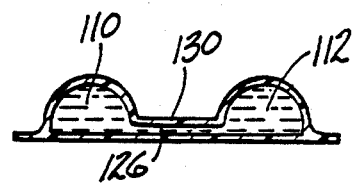
FIG. 10 is a sectional view taken along line 10—10 of FIG. 8.
Figure 9:
FIG. 9 is a sectional view taken along line 9—9 of FIG. 8.

Referring now to FIG. 8, there is shown a second embodiment of the device which is operable to draw two blood samples. The device includes a needle 108 which is set into a base member 106. An elastomeric tube 104 is mounted on the base member 106, the tube 104 being of two-part construction which provides side-by-side collection chambers 110 and 112. The device shown in FIG. 8 is used with a plug similar to that previously described. Each of the chambers 110 and 112 has a porous hydrophobic valve 114 and 116 disposed therein to separate the collection chambers 110 and 112 from associated sampling chambers 118 and 120. As previously noted, the tube 104 can be kinked at 122 and 124 to close the valves 114 and 116 to the passage of blood. The collection chambers 110 and 112 are interconnected by a cross passage 126. Mixing beads 128 may be disposed in one of the collection chambers. The chamber 112 having the mixing beads may be coated with an anticoagulant, while the chamber 110 is free of anticoagulant.

Figure 11:
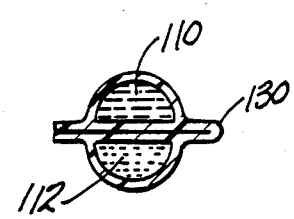
FIG. 11 is a sectional view similar to FIG. 10 but showing the device folded into a sealed condition.

The device operates as follows. A venous pressure sample is drawn into the chamber 110 through the needle 108 while the areas 22 and 124 are kinked. When the chamber 110 has filled with blood, the blood will then flow through the cross passage 126 into the second anticoagulant-coated chamber 112. When the chamber 12 is filled, blood flow stops and the device is withdrawn from the vein. In this manner, one whole blood sample is obtained, and one anticoagulated blood sample is also obtained, both from the same stick. The two halves of the device are connected by a plastic web 130 through which the cross passage 126 runs. As seen in FIG. 11, the two chambers 110 and 112 can be folded into back-to-back relationship by folding the web 130. The device can then be placed in the container tube, previously described, with the needle sealed and concurrently centrifuged therein. The two chambers, 110 and 112 can be separated from each other by severing the web 130 with a heated snip which will seal the cross passage 126 against leakage. Samples can be withdrawn from each chamber 110 and 112 as previously described.

Figure 12:
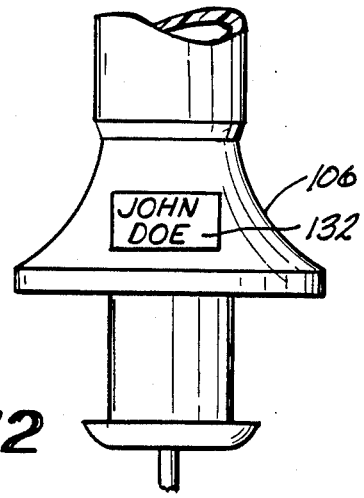
FIG. 12 is a fragmented elevational view of the base of the device illustrating a sample identification feature of the invention.

Referring now to FIG. 12, there is shown the outside surface of the base 106 of the device whereon a flat surface 132 has been molded to serve as an identification of the sample contained in the device. The surface 132 can be written on directly or can receive a gummed label bearing the identification of the sample.

It will be readily appreciated that the collecting device of this invention provides for improved performance since it may use a simply made 23 gauge needle attached to a plastic reservoir about the size of a common drinking straw. The hydrophobic filter allows passage of air only in one mode, allows passage of blood in another mode, and also allows passage of a tubular drawing instrument in yet another mode. The blood may be obtained by venipuncture and flows without the need of a syringe or vacuum. This prevents significant hemolysis of the sample since there is no excessive force applied to the blood. Collapse of the vein by creation of negative pressures is also thus prevented. This increases ease of sampling by allowing venous sampling from smaller veins as well as large veins. The provision of a separate sampling chamber in the device simplifies removal of blood samples therefrom. Both whole and anticoagulated blood can be sampled. The samples may be centrifuged in situ, and serum or plasma may be expressed into the sampling chamber after centrifugation. Serial samples may be taken. For example, a whole blood sample may be taken from the device, the remaining blood x-ray then be centrifuged in-situ, and a serum or plasma sample may then be taken from the device.

The device is designed to obtain samples of 200 to 1,000 microliters. The size and mode of operation of the device make it particularly non-traumatic to use. This is particularly important for use on children, chemotherapy patients, and others who need frequent venipuncture and access to small veins, and thereby freeing larger veins for intravenous therapy. Drawing of unnecessarily large blood samples, as is presently done, is avoided by the use of the device. The device can be disposed of in its original container without the risk of exposing the needle to others. The device is inexpensive to manufacture and simple and safe to use. This device is more compatible with current blood sampling instruments which only require small blood samples for analysis. Many present-day instruments use microliter amounts of blood for analysis. Use of this device should decrease the occurrence of hematomas and traumatic phlebitis. By avoiding the need to transfer aliquots of blood to different containers, the largest source of laboratory error is avoided, e.g., sample misidentification by mislabeling the different containers. The device has its own label which is at all times visible to the technician. The device may be used to obtain samples presently obtained by capillary puncture. The compound version of the device may be used to take anticoagulated blood as well as whole blood samples with a single stick.

Since many changes and variations of the disclosed embodiments of the device may be made without departing from the inventive concept, it is not intended to limit the invention otherwise than as required by the appended claims.

What is claimed is:

1. A device for utilizing venous blood pressure for drawing a blood sample, said device comprising:
   (a) a first tublar body providing a first collection reservoir for receiving the blood sample.
   (b) a needle mounted on one end of said tublar body for drawing the blood sample into said collection reservoir;
   (c) first valve means on the opposite end of said tubular body, said first valve means including a hydrophobic porous portion to allow flow of air from said collection reservior through said first valve means while blocking flow of blood from said collection reservoir through said first valve means, and said first valve means further including a passage formed in situ adjacent said hydrophobic porous portion which passage is operable to allow flow of blood from said collection reservoir through said first valve means; and
   (d) closure means for selectively closing said passage when a blood sample is drawn into said first collection reservoir through said needle.

2. The device of claim 1 wherein said tubular body further includes an integral sampling reservoir and said valve means is interposed between said collection reservoir and said sampling reservoir.

3. The device of claim 2 wherein said tubular body is elastomeric and said closure means is formed by a kink in said tubular body and said hydrophobic material is positioned in said kink.

4. The device of claim 3 wherein said hydrophobic material is in the form of an annular body having a through bore through which blood can flow when said kink is open.

5. The device of claim 3 further comprising a plug for sealing said needle after a blood sample is drawn.

6. The device of claim 5 wherein said tubular body includes a rigid base part secured thereto at the needle end thereof, and said plug and base part include interlocking means for locking said plug in needle-sealing engagement with said base part.

7. The device of claim 1 further comprising a second tubular body side-by-side and integral with said first tubular body, said second tubular body providing a second collection reservoir, and said second tubular body including second valve means operable in the same manner as said first valve means, and a blood flow passage connecting said first and second collection reservoir such that blood will flow into said second collection reservoir after said first collection reservoir is filled with blood.

8. A device for drawing a sample of blood solely by venous blood pressure, said device comprising:
   (a) an elastomeric tubular member forming a blood collection reservoir and an adjacent blood sampling reservoir;
   valve mens interposed between said collection reservoir and said sampling reservoir, said valve means including an air permeable portion and an in situ blood passage, and said valve means being operable, when said blood passage is closed, to allow flow of air while blocking flow of blood from said collection reservoir to said sampling reservoir through said valve means, and operable when said blood passage is open, to allow flow of blood from said collection reservoir to said sampling reservoir; and
   (c) a blood drawing needle mounted at the end of said collection reservoir remote from said valve means for drawing blood into said collection reservoir.

9. The device of claim 8 wherein said valve means includes a kink in said tubular member and an annular body of a hydrophobic material positioned in said tubular member in said kink, said kink being formed to close said valve means by bending said tubular member so as to position said sampling reservoir side-by-side with said collection reservoir and wherein said valve means is opened by pivoting said sampling reservoir about said kink away from said collection reservoir.

10. The device of claim 8 further comprising an elastomeric plug for embedment of said needle to seal said needle after a blood sample is drawn to prevent blood from being expressed from said collection reservoir through said needle and to provide said valve means as the sole means for enabling blood to be removed from said collection reservoir.

11. The device of claim 10 wherein said plug has a rounded outer end surface to adapt said device to be positioned in a centrifuge tube to enable in situ centrifugation of a blood sample in said collection reservoir.

12. The device of claim 10 further including means for irreversably locking said plug to said tubular member in sealing engagement with said needle.

13. A device for drawing a sample of blood solely by venous blood pressure, said device comprising:
   (a) an elastomeric tubular member forming a blood collection reservoir and an adjacent blood sampling reservoir;
   (b) a sleeve of hydrophobic material disposed in said tubular member between said reservoirs, said sleeve having a through bore forming a passage between said reservoirs;
   (c) a blood drawing needle disposed at an end of said collection reservoir remote from said sleeve, said needle providing means for drawing blood into said collection reservoir;
   (d) said tubular member being bent upon itself to position said sampling reservoir side-by-side with said collection reservoir and to form a kink in said tubular member and said sleeve to close said passage between said reservoirs, whereby said sleeve allows flow of air from said collection reservoir to said sampling reservoir during the drawing of a blood sample but blocks flow of blood from said collection reservoir to said sampling reservoir; and
   (e) said passage being operable to allow blood to pass therethrough by manipulating said tubular member to remove said kink.

14. The device of claim 13 further comprising an elastomeric plug for sealing said needle after a blood sample is drawn to prevent blood from being expressed from said collection reservoir via said needle whereby blood can only be removed from said collection reservoir through said passage.

15. The device of claim 14 wherein said tubular member and said elastomeric plug are provided with interlocking means to prevent said plug from being removed from said needle after engagement of said interlocking means.

16. The device of claim 14 wherein said plug has a rounded outer end surface to adapt said device for positioning in a centrifuge tube to enable in situ centrifugation of the blood sample in said collection reservoir.

17. The device of claim 13 further including means for releasably holding said sampling reservoir in side-by-side relationship with said collection reservoir.

18. In a blood sampling device, a valve comprising: an outer elastomeric tube which is impervious to both air and blood, and an inner sleeve formed from a hydrophobic material pervious to air but impervious to blood, said inner sleeve including a central through passage, said valve being closable to the passage of blood while allowing the passage of air by binding said outer tube and said inner sleeve sufficiently to form a kink in said tube and sleeve which closes said through passage, and said valve being openable to the passage of blood by unbending said tube and sleeve sufficiently to eliminate said kink and open said through passage.

19. A device for drawing a plurality of blood samples with a single venapuncture solely by venous blood pressure, said device comprising:
   (a) a first tubular molded plastic member forming a first blood collection reservoir;
   (b) a second tubular molded plastic member forming a second blood collection reservoir;
   (c) a molded plastic web integral with said first and second tubular members and interconnecting the latter so that said tubular members are disposed in side-by-side relationship;
   (d) vent means at one end of each of said collection reservoirs for venting air from said reservoirs during drawing of a blood sample, said vent means being operable to prevent the flow of blood therethrough;
   (e) a blood drawing needle at the end of said first collection reservoir opposite said vent means for drawing a blood sample into said first collection reservoir; and
   (f) a transverse passage extending through said web from said first collection reservoir to said second collection reservoir to provide means for transferring blood from said first collection reservoir to said second collection reservoir.

20. The device of claim 19 wherein said first and second plastic members each are formed with a common flat surface, and said device is folded about said web to bring said flat surfaces into face-to-face relationship to close said transverse passage after blood samples have been drawn into said first and second collection reservoirs.

* * * * *